US012594087B2

(12) United States Patent
Ein-Gal

(10) Patent No.: US 12,594,087 B2
(45) Date of Patent: Apr. 7, 2026

(54) PRECISE EXTRACORPOREAL SHOCKWAVES DELIVERY

(71) Applicant: Moshe Ein-Gal, Ramat Hasharon (IL)

(72) Inventor: Moshe Ein-Gal, Ramat Hasharon (IL)

( * ) Notice: Subject to any disclaimer, the term of this patent is extended or adjusted under 35 U.S.C. 154(b) by 0 days.

(21) Appl. No.: 18/408,759

(22) Filed: Jan. 10, 2024

(65) Prior Publication Data

US 2025/0221723 A1      Jul. 10, 2025

(51) Int. Cl.
*A61B 17/225*      (2006.01)
*A61B 17/00*      (2006.01)

(52) U.S. Cl.
CPC .. *A61B 17/225* (2013.01); *A61B 2017/00022* (2013.01); *A61B 2017/00141* (2013.01)

(58) Field of Classification Search
CPC ........ A61B 17/225; A61B 2017/00022; A61B 2017/00141
See application file for complete search history.

(56) References Cited

U.S. PATENT DOCUMENTS

| | | | | |
|---|---|---|---|---|
| 10,441,498 B1 * | 10/2019 | Zhu | ......................... | A61H 23/02 |
| 10,441,499 B1 * | 10/2019 | Zhu | ......................... | G10K 15/06 |
| 2014/0046246 A1 * | 2/2014 | Ferreira De Sa | ..... | A61M 37/00 |
| | | | | 604/22 |
| 2019/0290537 A1 * | 9/2019 | Engles | ..................... | A61N 7/00 |
| 2023/0095465 A1 * | 3/2023 | Burdette | .............. | A61B 8/4488 |
| | | | | 600/439 |
| 2023/0128152 A1 * | 4/2023 | Olson, Jr. | ............ | A61H 23/008 |
| | | | | 601/4 |
| 2024/0219224 A1 * | 7/2024 | Choi | ......................... | G01H 9/00 |
| 2024/0316369 A1 * | 9/2024 | Peters | ....................... | A61N 7/00 |

* cited by examiner

*Primary Examiner* — Baisakhi Roy
(74) *Attorney, Agent, or Firm* — Dekel Patent Ltd; David Klein

(57)      ABSTRACT

A method includes adjusting electrical energy of an extracorporeal shockwave generator, which delivers an entrance shockwave to a body that includes a target, in response to calculated or measured energy density at the target to deliver desired energy density to the target along a path. The calculated energy density at the target, called calculated target energy density, is derived from a calculated shockwave attenuation along the path to the target; and the measured target energy density is obtained by a sensor placed at the target or at a defined distance from the target.

10 Claims, 2 Drawing Sheets

ADJUST ELECTRICAL ENERGY OF EXTRACORPOREAL SHOCKWAVE GENERATOR, WHICH DELIVERS AN ENTRANCE SHOCKWAVE TO A BODY THAT INCLUDES A TARGET, IN RESPONSE TO CALCULATED OR MEASURED ENERGY DENSITY AT THE TARGET TO DELIVER DESIRED ENERGY DENSITY TO THE TARGET ALONG A PATH; THE CALCULATED ENERGY DENSITY AT THE TARGET, CALLED CALCULATED TARGET ENERGY DENSITY, IS DERIVED FROM A CALCULATED SHOCKWAVE ATTENUATION ALONG THE PATH TO THE TARGET; THE MEASURED TARGET ENERGY DENSITY IS OBTAINED BY A SENSOR PLACED AT THE TARGET OR AT A DEFINED DISTANCE FROM THE TARGET

DESIRED ENERGY DENSITY AT TARGET SELECTED SO THAT TISSUE ENERGY DENSITY DOES NOT EXCEED A LEVEL THAT COULD CAUSE AN UNDESIRABLE DAMAGE OR UNDESIRABLE RESULT

GENERATOR OUTPUT OF SHOCKWAVE GENERATOR DETERMINED BY: GENERATOR OUTPUT = TARGET ENERGY DENSITY/SHOCKWAVE GENERATOR CONVERSION/TARGET ATTENUATION, WHEREIN THE TARGET PATH ATTENUATION IS CALCULATED BY CASCADING THE RESPECTIVE ATTENUATION VALUES OF THE TISSUE SEGMENTS OF THE SHOCKWAVE ON ITS PATH TO THE TARGET

OR GENERATOR OUTPUT OF SHOCKWAVE GENERATOR DETERMINED BY: GENERATOR OUTPUT = TARGET ENERGY DENSITY/TARGET CONVERSION

TARGET PATH ATTENUATION PARTIALLY CONFIRMED BY CALCULATING EXIT ENERGY DENSITY AND COMPARING RESULT TO MEASURED VALUE

MEASURING TARGET ENERGY DENSITY DONE BY TRANSDUCER SENSOR PLACED IN THE TARGET VICINITY OR IN OR ON A NEEDLE OR CATHETER

SHOCKWAVES USED TO FRAGMENT CALCIFICATION OR PLAQUE IN A BODY LUMEN

GENERATOR CONFIGURED TO DELIVER SHOCKWAVES BETWEEN RIBS OF PATIENT

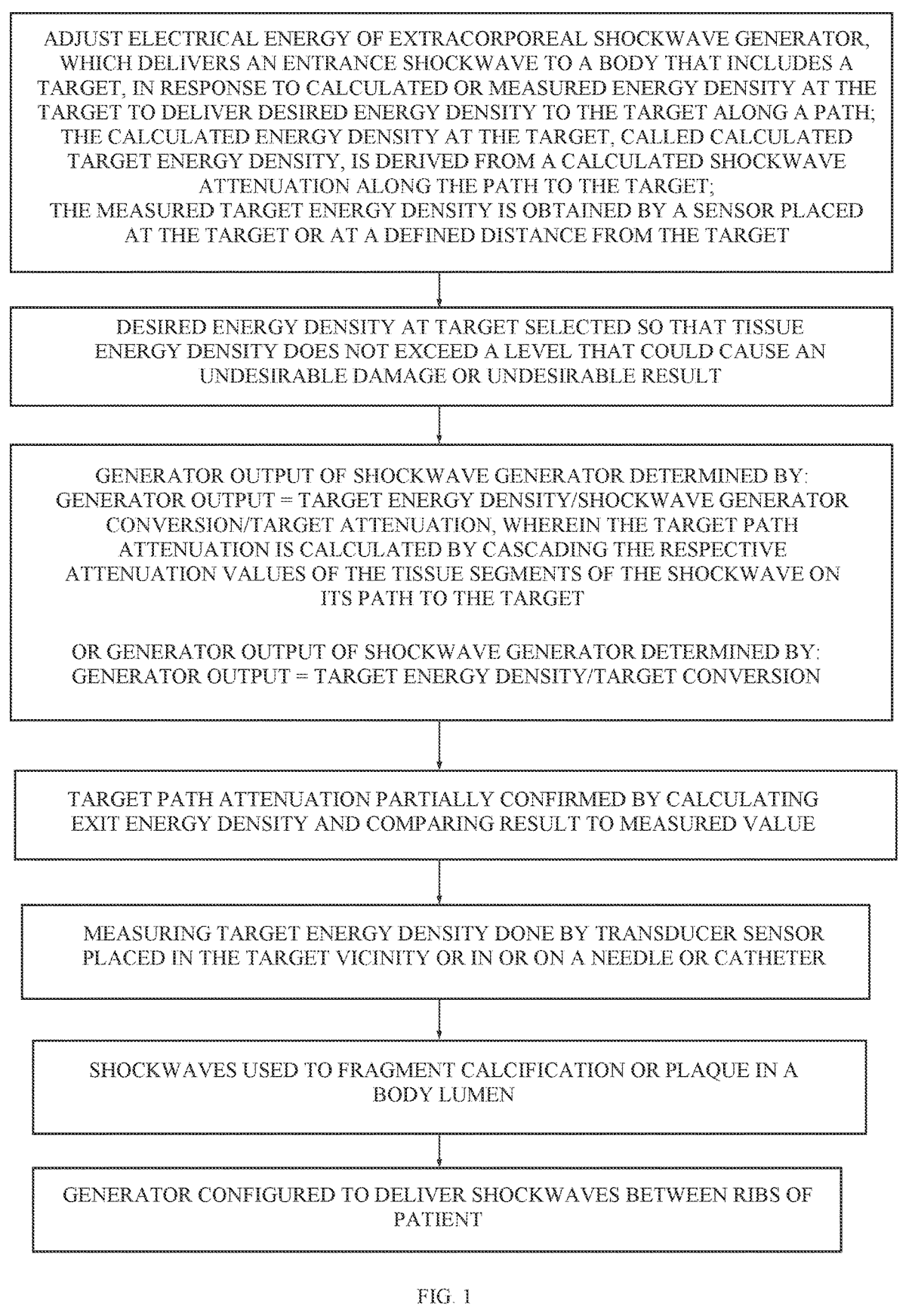

ADJUST ELECTRICAL ENERGY OF EXTRACORPOREAL SHOCKWAVE GENERATOR, WHICH DELIVERS AN ENTRANCE SHOCKWAVE TO A BODY THAT INCLUDES A TARGET, IN RESPONSE TO CALCULATED OR MEASURED ENERGY DENSITY AT THE TARGET TO DELIVER DESIRED ENERGY DENSITY TO THE TARGET ALONG A PATH; THE CALCULATED ENERGY DENSITY AT THE TARGET, CALLED CALCULATED TARGET ENERGY DENSITY, IS DERIVED FROM A CALCULATED SHOCKWAVE ATTENUATION ALONG THE PATH TO THE TARGET; THE MEASURED TARGET ENERGY DENSITY IS OBTAINED BY A SENSOR PLACED AT THE TARGET OR AT A DEFINED DISTANCE FROM THE TARGET

DESIRED ENERGY DENSITY AT TARGET SELECTED SO THAT TISSUE ENERGY DENSITY DOES NOT EXCEED A LEVEL THAT COULD CAUSE AN UNDESIRABLE DAMAGE OR UNDESIRABLE RESULT

GENERATOR OUTPUT OF SHOCKWAVE GENERATOR DETERMINED BY: GENERATOR OUTPUT = TARGET ENERGY DENSITY/SHOCKWAVE GENERATOR CONVERSION/TARGET ATTENUATION, WHEREIN THE TARGET PATH ATTENUATION IS CALCULATED BY CASCADING THE RESPECTIVE ATTENUATION VALUES OF THE TISSUE SEGMENTS OF THE SHOCKWAVE ON ITS PATH TO THE TARGET

OR GENERATOR OUTPUT OF SHOCKWAVE GENERATOR DETERMINED BY: GENERATOR OUTPUT = TARGET ENERGY DENSITY/TARGET CONVERSION

TARGET PATH ATTENUATION PARTIALLY CONFIRMED BY CALCULATING EXIT ENERGY DENSITY AND COMPARING RESULT TO MEASURED VALUE

MEASURING TARGET ENERGY DENSITY DONE BY TRANSDUCER SENSOR PLACED IN THE TARGET VICINITY OR IN OR ON A NEEDLE OR CATHETER

SHOCKWAVES USED TO FRAGMENT CALCIFICATION OR PLAQUE IN A BODY LUMEN

GENERATOR CONFIGURED TO DELIVER SHOCKWAVES BETWEEN RIBS OF PATIENT

FIG. 1

PRECISE EXTRACORPOREAL SHOCKWAVES DELIVERY

FIELD OF THE INVENTION

The present invention generally relates to methods and apparatus for medical treatment of pathological conditions by means of acoustic shock waves, and particularly to methods and apparatus for regulating delivery of extracorporeal shockwaves by adjusting operational parameters of the extracorporeal shockwaves based on measurement and/or calculation of energy density and attenuation of the shockwaves.

BACKGROUND OF THE INVENTION

Extracorporeal shock wave therapy (ESWT) is the non-surgical treatment of medical conditions using acoustic shock waves. Acoustic shock waves for ESWT may be generated by a variety of methods, such as electrohydraulic, electromagnetic, or piezoelectric.

For example, application of extracorporeal shockwaves for urinary stones disintegration is a well-established procedure. A shockwaves series is produced by an extracorporeal generator, coupled to a patient, and focused on a target stone. Fluoroscopic or ultrasonic imaging localize the target and enables generator positioning for focusing the shockwaves on the target. The generator's electrical output determines the shockwave's energy density at the target based on the energy density entering the body and the tissue attenuation.

The respective ranges of the target pulse energy and number of applied pulses may be wide; a higher pulse energy is correlated with a shorter disintegration time. The disintegration process is monitored in real-time and may be stopped upon completion.

U.S. Pat. No. 5,078,144 describes a method for urinary stone disintegration using an extracorporeal ultrasonic (not shockwaves) system where the ultrasonic generator's position is determined by measuring the ultrasonic intensity (energy per unit time) at the target vicinity. The generator is moved, and its position is deemed acceptable when the ultrasonic intensity exceeds a pre-determined value, irrespective of possible exposure of neighboring tissue to higher intensities.

U.S. Pat. No. 10,702,293 describes shockwaves fragmentation of calcified plaque in a blood vessel. Imaging is used to place an intraluminal shockwaves generator to face the calcification (plaque) in the blood vessel. The number of shockwaves pulses delivered to the plaque and the energy per pulse are controlled: they are sufficiently high for fragmenting the plaque and sufficiently low for avoiding fragments from entering the blood stream.

SUMMARY OF THE INVENTION

The present invention seeks to provide improved methods and apparatus for regulating delivery of extracorporeal shockwaves by adjusting operational parameters of the extracorporeal shockwaves based on measurement and/or calculation of energy density and attenuation of the shockwaves, as is described more in detail hereinbelow.

The present invention may be used in a wide variety of medical procedures, such as but not limited to, methods for treating cardiovascular problems such as calcifications or occlusions in blood vessels, heart valves and other tissues, calcifications or stones in other tissues, such as urinary stone disintegration, kidney stones, and others, pathological conditions associated with bones and musculoskeletal environments, as well as soft tissue, such as for treating diabetic foot ulcers, pressure sores, cutaneous, subcutaneous, and fascial geographic tissue injuries, defects, or deficits, degenerative joint diseases, soft tissue injuries, decalcification, osteochondronatosis and enchondromatosis, facet osteoarthritis, abnormal neuromuscular pain and abnormalities of development.

The invention encompasses any kind of shockwave or pulsed acoustic waves generation. For example, the invention may also be carried out using histotripsy. The underlying mechanism of histotripsy is fundamentally different from thermal HIFU (high intensity focused ultrasound), relying instead on a mechanical effect at the cellular level to destroy tissue. In contrast to thermal HIFU which uses continuous or long bursts of ultrasound at moderately high intensity and high duty cycle to heat tissue, histotripsy uses short acoustic bursts (microseconds in length) with a low duty cycle to minimize heating, and higher peak pressure amplitudes to generate acoustic cavitation from endogenous gas in tissues. Acoustic cavitation is the generation, oscillation, and collapse of microbubbles activated by acoustic energy.

There is thus provided in accordance with a non-limiting embodiment of the present invention a method including adjusting electrical energy of an extracorporeal shockwave generator, which delivers an entrance shockwave to a body that includes a target, in response to calculated or measured energy density at the target to deliver desired energy density to the target along a path; wherein the calculated energy density at the target, called calculated target energy density, is derived from a calculated shockwave attenuation along the path to the target; and the measured target energy density is obtained by a sensor placed at the target or at a defined distance from the target.

In accordance with a non-limiting embodiment of the present invention the desired energy density at the target is selected so that tissue energy density does not exceed a level that could cause an undesirable damage or undesirable result.

In accordance with a non-limiting embodiment of the present invention a generator output of a generator that generates the shockwaves is determined by:

generator output=target energy density/shockwave generator conversion/target attenuation, wherein the target path attenuation is calculated by cascading the respective attenuation values of the tissue segments of the shockwave on its path to the target.

In accordance with a non-limiting embodiment of the present invention the target path attenuation is partially confirmed by calculating the exit energy density and comparing the result to a measured value.

In accordance with a non-limiting embodiment of the present invention a generator output of a generator that generates the shockwaves is determined by:

generator output=target energy density/target conversion

In accordance with a non-limiting embodiment of the present invention measuring the target energy density is done by a transducer placed in the target vicinity.

In accordance with a non-limiting embodiment of the present invention the transducer is in or on a needle or a catheter.

In accordance with a non-limiting embodiment of the present invention the shockwaves are used to fragment calcification or plaque in a body lumen.

BRIEF DESCRIPTION OF THE DRAWINGS

The present invention will be understood and appreciated more fully from the following detailed description, taken in conjunction with the drawing in which:

FIG. 1 is a simplified block diagram of a method for regulating delivery of extracorporeal shockwaves, in accordance with a non-limiting embodiment of the present invention.

DETAILED DESCRIPTION OF EMBODIMENTS

Figure 2:
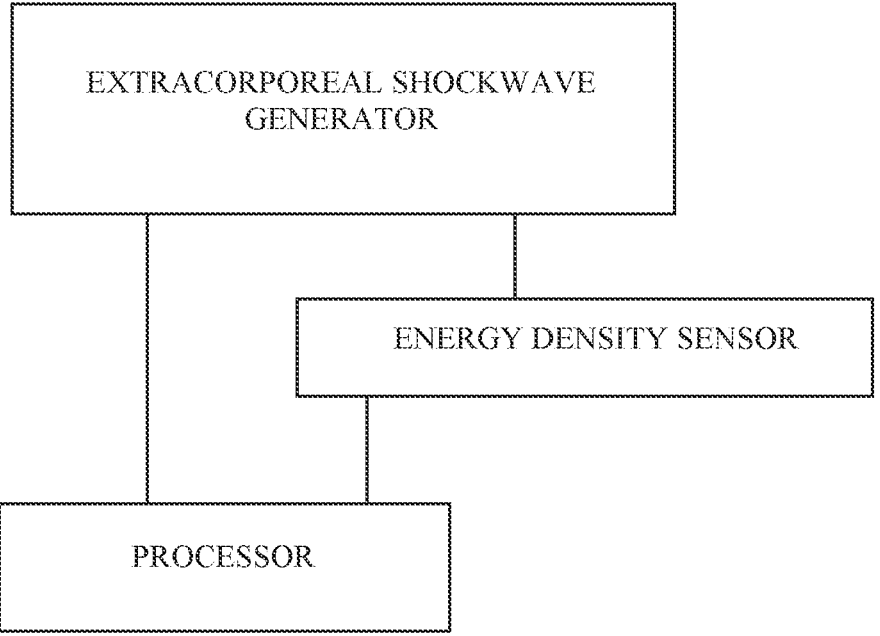
FIG. 2 is a simplified block diagram of apparatus for regulating delivery of extracorporeal shockwaves, in accordance with a non-limiting embodiment of the present invention.

Reference is now made to FIG. 1, which illustrates a method for regulating delivery of extracorporeal shockwaves, in accordance with a non-limiting embodiment of the present invention.

It is noted that the terms pressure pulses, pressure waves, and shockwaves are used interchangeably.

The method includes delivery of shockwaves to a target by an extracorporeal generator operable to generate shockwaves (such as but not limited to, by converting electrical energy to shockwaves pulses), (optionally focus the shockwaves), and deliver the shockwaves (such as but not limited to, focused shockwave pulses) to a target inside a body.

As in conventional extracorporeal shockwaves lithotripsy (ESWL), imaging, such as but not limited to, fluoroscopic or ultrasound imaging, may be used for target localization and/or for characterization of attenuating tissue segments. In the present invention, the shockwave energy density at the target is controlled with high precision by adjusting the generator's output, opening a door for treatments requiring precise energy delivery to the target, such as fragmentation of calcified plaque.

Patient-dependent attenuation of the shockwaves propagating toward the target is compensated for by adjusting operational parameters of the generator output. Proper adjustment requires the calculation of the attenuation of the shockwaves or the measurement of the energy density at the target (or its vicinity), obtained in response to varying generator output. The generator's operational parameters include, without limitation, frequency (which may be 60 shockwaves per minute, or 90 shockwaves per minute, or 120 shockwaves per minute, or synchronized to the heartbeat, for example), generator's energy level of an output pulse (which may be 20-500 J), the number of pulses (which may be 20-4,000), and other parameters.

The procedure may include:

a) calculating the attenuation of the shockwaves and using the relationship between the generator electrical output and the produced energy density, or b) measuring the energy density at the target (or at the target's vicinity, that is, an area at a defined distance to the target) in response to the shockwave generator output, and c) adjusting the shockwave generator output—using the above calculation and/or measurement—to obtain the required energy density at the target. The pre-determined energy density may be constrained for avoiding undesirable damage or undesirable result. The desired energy density at the target may be specified with a tolerance of no more than 10%, preferably 5% of the desired energy density.

The following terms apply:

Energy density: the shockwave energy per unit area

Entry or Exit energy density: the shockwave energy density at the entry to or the exit from the treated body containing the target, respectively.

Target energy density: the shockwave energy density at the target.

Vicinity energy density: the shockwave energy density at the target vicinity, that is, an area at a defined distance to the target.

Target Path Attenuation: the calculated ratio of Target energy density to Entry energy density.

Exit Path Attenuation: the ratio of Exit energy density to Entry energy density.

Generator Output: the electrical pulse energy supplied by the generator.

Generator Conversion: the measured ratio of Entry energy density to Generator Output.

Target Conversion: the measured ratio of target energy density to generator output.

The generator output for obtaining the required target energy density (TED) may be obtained by measuring the generator conversion (GC), calculating the target path attenuation (TPA), and using the following expression:

$$\text{Generator output} = \text{TED} \cdot \text{GC} / \text{TPA} \qquad (1)$$

The target path attenuation may be calculated by cascading the respective shockwave attenuation values of the respective tissue segments of the on its path to the target. Attenuation data of various tissues are available in the literature. The result of the calculated TPA may be partially confirmed by calculating the exit energy density using the same attenuation data, and comparing the result to the measured value.

Alternatively, the required generator output may be obtained by measuring the target conversion (TC) and using the expression:

$$\text{Generator output} = \text{TED} / \text{TC} \qquad (2)$$

The desired target conversion (TC) may be obtained by varying the generator's output and measuring the respectively obtained shockwaves energy densities at the target (TED) until the desired energy density is obtained. The measurement may use a transducer that is insertable into the target (or its vicinity) on a tip of a piercing needle, or is guided to the target (or its vicinity) via a trans-luminal catheter.

Deriving the required Generator output, i.e., by measuring the target and generator conversions (TC and GC, respectively), or by calculating the target path attenuation (TPA) may be done in a preparatory session prior to the shockwave treatment session, simplifying the treatment session like ESWL.

What is claimed is:

1. A method comprising:

adjusting electrical energy of an extracorporeal shockwave generator, which delivers an entrance shockwave to a body that includes a target, said entrance shockwave having an entry energy density at entry to the body, in response to calculated or measured energy density at entry to the target to deliver desired energy density to the target along a path; wherein the calculated energy density at entry to the target, called calculated target energy density, defined as shockwave energy per unit area at the target, is derived from a calculated shockwave attenuation along the path to the target; and the measured target energy density is obtained by a sensor placed at the target or at a distance from the target; and after adjusting the electrical energy of said extracorporeal shockwave generator, using said extracorporeal shockwave generator to deliver shockwaves to said target to treat a medical condition in said body, wherein adjusting the electrical energy of said extracorporeal shockwave generator provides more precise delivery of the shockwaves; and wherein a generator output of a generator that generates the shockwaves is determined by:

Generator output=target energy density/target conversion, wherein the target conversion is obtained by varying the generator output and measuring respectively obtained shockwaves energy densities at the target until a desired energy density is obtained.

2. The method according to claim 1, wherein the desired energy density at entry to the target is selected so that tissue energy density does not exceed a level that could cause an undesirable damage or undesirable result.

3. The method according to claim 1, wherein measuring the target energy density is done by said sensor placed in the target vicinity.

4. The method according to claim 3, wherein the sensor is in or on a needle or a catheter.

5. The method according to claim 3, wherein said sensor comprises an energy density sensor.

6. The method according to claim 1, wherein the shockwaves are used to fragment calcification or plaque in a body lumen.

7. The method according to claim 1, wherein the generator is configured to deliver shockwaves between ribs of a patient.

8. A method comprising:

adjusting electrical energy of an extracorporeal shockwave generator, which delivers an entrance shockwave to a body that includes a target, said entrance shockwave having an entry energy density at entry to the body, in response to calculated or measured energy density at entry to the target to deliver desired energy density to the target along a path;

wherein the calculated energy density at entry to the target, called calculated target energy density, defined as shockwave energy per unit area at the target, is derived from a calculated shockwave attenuation along the path to the target; and the measured target energy density is obtained by a sensor placed at the target or at a distance from the target; and after adjusting the electrical energy of said extracorporeal shockwave generator, using said extracorporeal shockwave generator to deliver shockwaves to said target to treat a medical condition in said body, wherein adjusting the electrical energy of said extracorporeal shockwave generator provides more precise delivery of the shockwaves, wherein a generator output of a generator that generates the entry shockwaves is determined by:

Generator output=TED*GC/TPA wherein TED is said calculated target energy density, GC is generator conversion, which is a measured ratio of said entry energy density to generator output, and TPA is target path attenuation, which is calculated by cascading respective attenuation values of tissue segments of the entry shockwave on its path to the target.

9. The method according to claim 8, wherein the target path attenuation is confirmed by calculating an exit energy density, which is shockwave energy density at an exit of the target, and comparing the result to a measured value.

10. An extracorporeal shockwave system comprising:

an extracorporeal shockwave generator configured to deliver an entrance shockwave to a body that includes a target, said entrance shockwave having an entry energy density at entry to the body;

an energy density sensor; and a processor in communication with said extracorporeal shockwave generator and said energy density transducer, wherein said processor is configured to adjust electrical energy of said extracorporeal shockwave generator, in response to calculated or measured energy density at entry to the target, to deliver desired energy density to the target along a path, wherein the calculated energy density at entry to the target, called calculated target energy density, defined as shockwave energy per unit area at the target, is derived from a calculated shockwave attenuation along the path to the target, said shockwave attenuation being calculated as a ratio of the target energy density to said entry energy density, and the measured target energy density is obtained by said energy density sensor placed at the target or at a distance from the target.

* * * * *